United States Patent [19]
Capuano et al.

[11] Patent Number: 5,693,538
[45] Date of Patent: Dec. 2, 1997

[54] SYSTEM AND METHOD FOR MONITORING VOLATILE SPECIES IN LIQUIDS

[75] Inventors: Italo A. Capuano, Orange; Kenneth E. Creasy, Wallingford, both of Conn.

[73] Assignee: Olin Corporation, Cheshire, Conn.

[21] Appl. No.: 521,782

[22] Filed: Aug. 31, 1995

[51] Int. Cl.[6] .................................................. G01N 33/18
[52] U.S. Cl. .................... 436/181; 73/19.1; 73/23.41; 422/83; 422/89
[58] Field of Search ................... 210/141, 198.2, 210/656, 739, 194, 175, 188, 774, 805; 422/63, 83, 89; 73/19.01, 19.02, 19.1, 23.41, 23.42, 61.41, 61.43, 863.2; 96/101, 103, 105, 106; 436/161, 178, 180, 181; 95/82, 89

[56] References Cited

U.S. PATENT DOCUMENTS 5,222,032  6/1993  Fleming .................... 73/19.1
5,258,057  11/1993  Baykut .................... 96/105
5,266,496  11/1993  Dacruz .................... 73/19.1
5,441,700  8/1995  Markelov .................... 422/83

OTHER PUBLICATIONS

American Laboratory, May 1989, "On-line headspace GC" by D. D. Soleta, pp. 21–24.

*Primary Examiner*—Joseph W. Drodge
*Attorney, Agent, or Firm*—Dale Lynn Carlson; Wiggin & Dana

[57] ABSTRACT

A system and method for monitoring a volatile species in a liquid in which liquid is fed from its source to a head space chamber. The flow of liquid to the chamber is then halted, the volatile species allowed to escape into the gaseous phase above the liquid, and a carrier gas is caused to flow to the chamber and over the liquid to carry the gaseous phase of the species to a detector while the flow of the liquid to the head space chamber is halted. The liquid may be under pressure at the point in the source from which it is withdrawn into the system and returned to the source at a point also under pressure.

20 Claims, 4 Drawing Sheets

SYSTEM AND METHOD FOR MONITORING VOLATILE SPECIES IN LIQUIDS

BACKGROUND OF THE INVENTION

1. Field of the Invention

This invention relates generally to the monitoring of volatile species in liquids. More particularly, this invention relates to a system and method for the monitoring of volatile species in liquids which utilizes a head space chamber.

2. Background

There are many instances when it is desirable to monitor the presence and amount of a volatile species that may be present in a particular liquid. Such instances may arise, for example, during the course of chemical processes where the presence of a particular volatile species, or a certain amount of such species, may be deleterious to the course of the process or the final product being produced. The need may also arise in chemical process where the presence of hazardous or toxic substances in a process stream must be monitored so that appropriate action may be take to prevent their release.

In the monitoring of such processes, it is desirable that the sample be taken directly from the process stream into the sampling apparatus. This permits rapid sequential analysis so that the process stream may be continuously monitored. Thus the apparatus used for sampling must be capable of being used on-line in a substantially continuous mode so that the liquid in the process stream may be continuously monitored during the process.

An example of a process where it is desirable to provide continuous monitoring include the production of isocynates by the reaction of phosgene with amines wherein it is desirable to monitor the presence of the phosgene in the organic solvent to maintain the proper level thereof. Another example wherein monitoring may be desirable is in pollution control such as the treatment of waste water. It may be desirable to monitor the presence of benzene and other toxic substances in the flow of waste water to a treatment facility.

Monitoring systems which use a stripper or sparging system to separate the volatile species from the liquid sample as by bubbling a gas through the liquid are not completely satisfactory. The use of a sparging or stripping gas dilutes the sample which ultimately goes to the detector. Also, in the use of sparging systems, the species will tend to redissolve back into the liquid as the sparging gas passes through the liquid. As a result of the dilution and redissolving, lower concentrations of the species in the liquid sample may not be able to be detected.

Also, in many of these processes, the liquid in the process at the point at which it must be sampled is under pressure. In the sparging systems, the liquid sample must be at atmospheric pressure in the sparging unit. In many cases, the sample liquid cannot be returned to a drain, but must be returned to the process stream at a point where the process is under pressure. This presents a problem. Without extra equipment the flow in the return line will back up into the sampling apparatus instead of the excess liquid sample being returned thereto.

The use of a "head space column" in on-line gas chromatography is disclosed in the article "On-line headspace GC" appearing in the May 1989 issue of *American Laboratory*, pages 21–24. In the system disclosed therein, a constant sample flow is fed to a headspace column which is filled with perforated saddle packing to provide a large surface area. As the sample drips down the head space column, a nitrogen sparge entering the bottom of the column flows upward and becomes enriched with the vapor from the sample. The nitrogen sparge containing the vapor exits the top of the column and then is passed to a sample loop on a ten-port valve. Activation of the ten-port valve introduces an aliquot of the nitrogen sparge into the process gas chromatograph for analysis. Nitrogen is used as the carrier gas for carrying the aliquot of the nitrogen sparge through a gas chromatograph provided with a detector.

While such a system may be satisfactory for some applications, it is not completely satisfactory for the reasons mentioned above since the system relies upon a sparging gas to become enriched with the species as it passes through the column to separate the species from the liquid. Additionally, the system disclosed in the publication cannot return the excess liquid sample to the process stream at a point wherein the stream is under pressure without additional modification.

SUMMARY OF THE INVENTION

In view of the above, it is an object of the present invention to provide an improved system and method for the monitoring of volatile species in liquids.

Another object of the present invention to provide an improved system and method for the monitoring of a volatile species in liquids which has increased analysis sensitivity.

Yet another object of the present invention to provide an improved system and method for the monitoring of a volatile species in liquids wherein the liquid containing the volatile species to be monitored is taken from a process stream.

Still another object of the present invention is to provide an improved system and method for the monitoring of volatile species in a liquid wherein a sample of the liquid containing the volatile species is taken from a process stream that is under pressure and returned to the process stream at a point also under pressure.

A still further object of the present invention is to provide an improved system and method for the monitoring volatile species in a liquid which has universal application and which is relatively simple and inexpensive to construct.

These and other objects and advantages of the present invention may be achieved through the provision of a method of monitoring a volatile species in a liquid which comprises providing a flow of the liquid containing the volatile species to be monitored from its source to a head space chamber, interrupting the flow of said liquid to said chamber to provide a volume of liquid in said chamber and permitting the volatile species to escape from said liquid in said chamber into the gaseous phase while in said chamber, and subsequently sweeping a carrier gas over the surface of said liquid volume while said liquid flow is interrupted to carry the gaseous species to a detector for monitoring the volatile species.

A system for the monitoring a volatile species in a liquid according to the present invention may comprise a head space chamber in which the volatile species in the liquid escape from the liquid into a gaseous phase above the liquid, a first valve arrangement for controlling the flow of the liquid to be sampled from its source to said head space chamber, a detector for detecting the presence of the species in gaseous form, a source of a carrier gas, a second valve arrangement for controlling the flow of said carrier gas to said head space chamber, and a controller for actuating the first valve arrangement to permit flow of said liquid from its source to said head space chamber and thereafter halting the flow thereto, and actuating the second valve arrangement after the halting of the flow of the liquid by said first valve arrangement to permit flow of said carrier gas to said head space chamber to carry the gaseous phase of the volatile species to said detector.

BRIEF DESCRIPTION OF THE DRAWINGS

The objects and advantages of the present invention will become more apparent by reference to the following detailed description and to the accompanying drawings in which.

DETAILED DESCRIPTION

Figure 1:
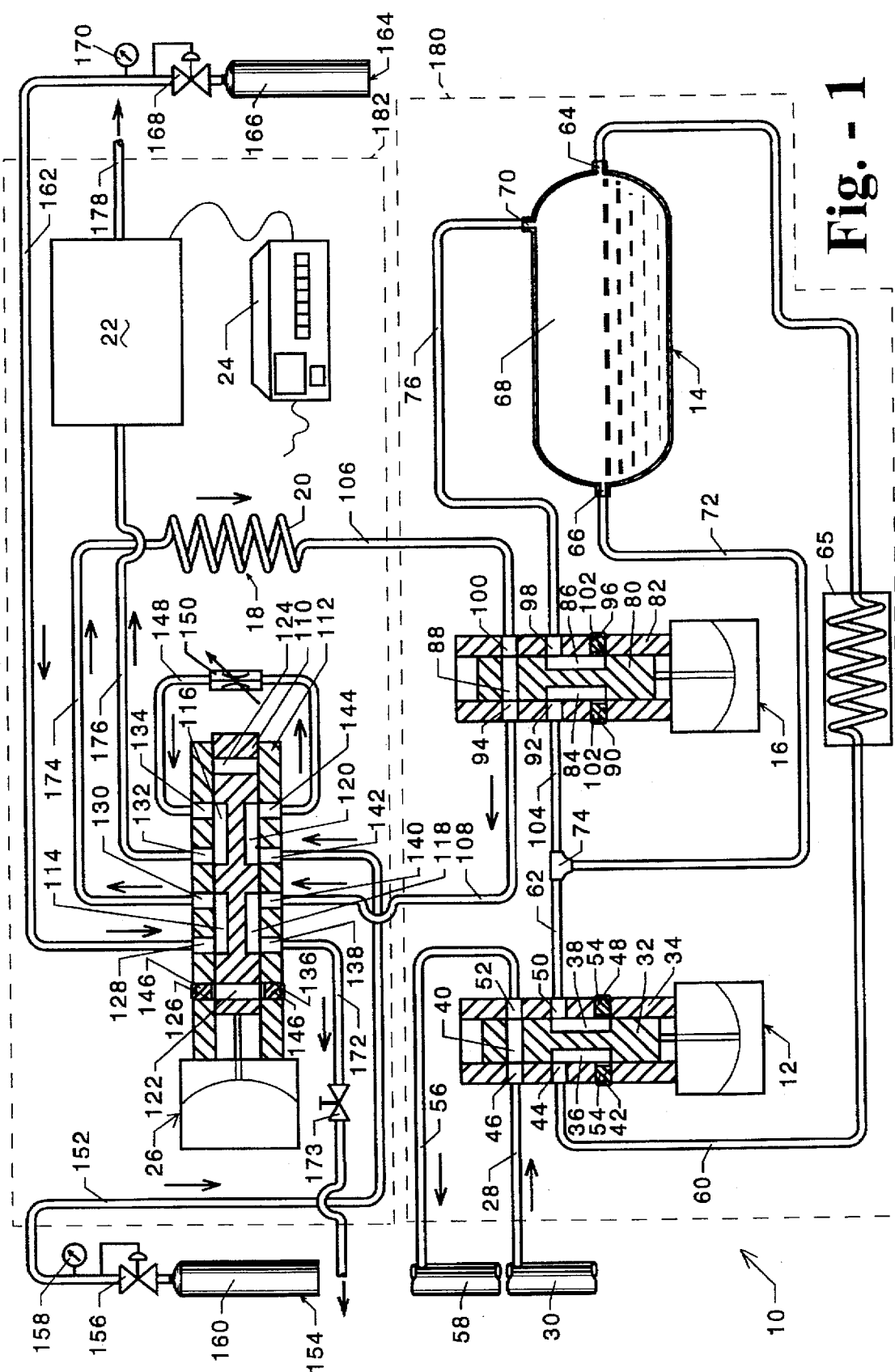
FIG. 1 is a schematic diagram of a monitoring system incorporating the principals of the present invention and showing the position of the valves at one stage of the operation of the system.

Referring to the drawings, and particularly FIG. 1, there is shown a schematic diagram of a system 10 for monitoring a volatile species in a liquid. The system 10 may be used to monitor a particular species whenever a liquid sample contains species which can be volatilized from its matrix. The system 10 is also adapted to monitor a volatile species in a liquid when the liquid containing the volatile species must be withdrawn from and returned to a process at a point where the liquid is under pressure.

In general, the system 10 includes a sample inlet control valve 12 for controlling the flow of a liquid sample from the process, a head space chamber 14 in which the sample from the process is temporarily held to permit the volatile species to escape from the liquid matrix into a gaseous phase and reach equilibrium, a fluid control valve 16 which directs flow of a carrier gas to the head space chamber 14 to carry the gaseous phase in the head space chamber to a separation unit 18 such as a chromatographic column 20 for physically separating the subject species and then to a detector 22 for detecting and measuring the presence and amount of the particular species. A microprocessor 24 may be provided to control the sampling operation and receive signals from the detector 22. A backflush control valve 26 may be provided in conjunction with the chromatographic column 20 to control the flow of a backflush gas to the column 20 and also provide for the periodic flushing of the detector 22 with a gas during the intervals between sampling. As an alternative, the system 10 may be set up so that the carrier gas containing the gaseous species passes directly to the detector 22.

More specifically, a sample input line 28 is connected to a source such as a line 30 of the process stream, or other suitable portion of the process equipment, containing the liquid to be sampled. The present invention is particularly adapted to the taking of a liquid sample from a process where the liquid in the process is under pressure, i.e., a pressure greater than atmospheric pressure. Such pressure may typically be 5 psig or greater and may be in the range of from about 5 to about 100 psig. Thus, the pressure of the liquid in the line 30 at the point the sample input line 28 is connected thereto may be greater than atmospheric pressure.

The sample input line 28 is connected to the sample inlet control valve 12. This valve 12 may be any suitable type of electrically controlled, on-off valve which can be controlled by the microprocessor 24 or other control device. Preferably, the valve 12 is a modified, commercially available, six-port slider plate valve which is pneumatically actuated between a deactive position and an activated position. A solenoid valve (not shown), controlled by the microprocessor 24, may control the supply of pneumatic fluid such as instrument air to the valve 12 to cause the movement of the valve between its two positions.

The sampling valve 12 may include a slider plate 32 movable in a body 34 between the two positions of the valve. The slider plate 32 may include a first axially extending groove or passage 36 in one surface of the slider plate 32. A second groove or passage 38 may extend axially in the opposite surface of the slider plate 32 as shown. A through-bore or passage 40 extends between the two surfaces of the slider plate 32.

The body 34 of the sample inlet control valve 12 may include six ports 42, 44, 46, 48, 50 and 52. The ports 42, 44 and 46 are positioned in one side of the body 34 and the ports 48, 50 and 52 are positioned in the opposite side of the body 34 as shown.

The valve 12 is modified by eliminating or blocking the two ports 42 and 48 which are diametrically opposite to each other as shown. These ports 42 and 48 may be rendered inactive by inserting suitable plugs 54 therein.

In the deactive or "off" position of the valve 12, as shown in FIG. 1, the passage 36 connects the ports 42 and 44, and thus is inactive since port 42 is plugged. The passage 38 connects the ports 48 and 50, and is also inactive in the "off" position since the port 48 is plugged. The through-bore or passage 40 in the slider plate 32 connects the ports 46 and 52.

Figure 2:
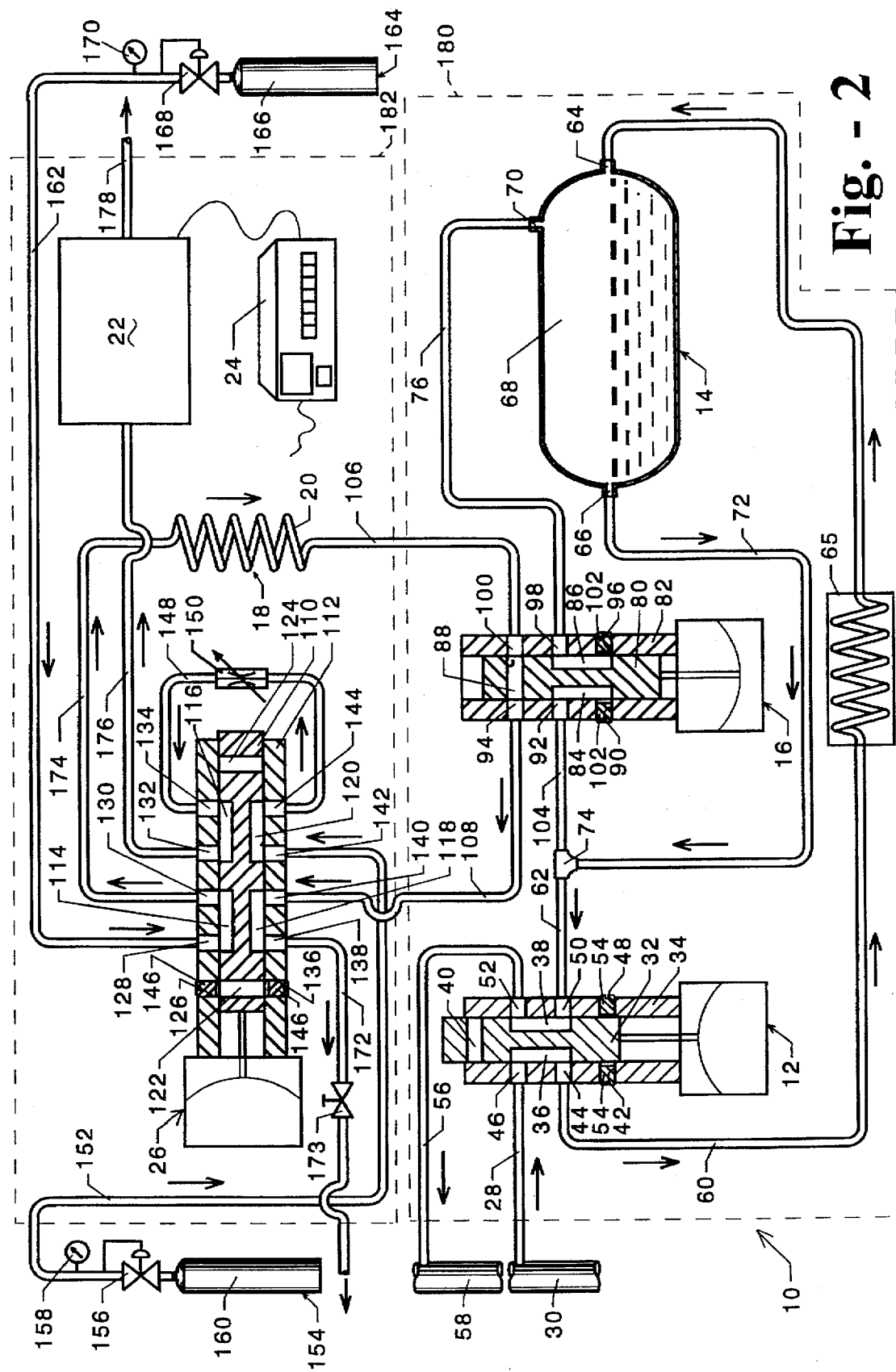
FIG. 2 is a schematic diagram of the monitoring system shown in FIG. 1 showing the positions of the valves and flow through the system during another stage of operation of the system.

When the valve 12 is actuated into its activated, or "on" position, shown in FIG. 2, the slider plate 32 is extended outwardly, upwardly as viewed in the drawings, so that the passage 36 connects the ports 44 and 46 and passage 38 connects the ports 50 and 52. The ports 42 and 48 are blocked and the through-bore or passage 40 is not in communication with any of the ports as shown.

The sample input line 28 is connected to the port 46 of the sample inlet control valve 12. A sample return line 56 is connected at one end to the port 52 of the valve 12. The other end of the sample return line 56 is connected to the source of the liquid such as a line 58 or other suitable portion of the process equipment at a point which is at a lower pressure than the point from which the sample is taken, but which may be greater than atmospheric pressure. A sample feed line 60 is connected to the port 44 of the valve 12 and leads to the head space chamber 14. A sample out-feed line 62 is connected to the port 50 of the valve 12.

The sample feed line 60 is connected to an inlet port 64 of the head space chamber 14. The line 60 contains a heat exchanger 65 which serves to heat the incoming liquid sample as it passes to the head space chamber 14 from the sample inlet control valve 12.

The head space chamber 14 is provided with a liquid outlet port 66 at its end opposite the inlet port 64. The outlet port 66 is vertically spaced downward from the inside top of the chamber 14 to provide a head space area 68 above the liquid level for the volatile species in the liquid phase to pass into a gaseous phase above the liquid. A gas outlet port 70 is positioned in the upper portion of the head space chamber 14 vertically above the horizontal plane of the axis of the liquid outlet port 66, and adjacent the end of the chamber 14 containing the liquid inlet port 64. Specifically, the gas outlet port 70 is in the uppermost portion of the chamber 14 as shown.

Preferably, the head space chamber 14 may be formed from an elongated tube or other elongated receptacle which has its axis of elongation in a horizontal plane which provides a relatively large exposed surface area of the liquid in relationship to its volume when the liquid is contained therein. The relatively large exposed surface area provides for a more rapid passage of the species into the headspace area 68.

The liquid outlet port 66 of the head space chamber 14 is connected to a sample feed return line 72 which in turn is connected a tee 74 connected to the sample out-feed line 62. The gas outlet port 70 of the head space chamber 14 has a gas flow line 76 connected thereto which is connected to the fluid control valve 16.

The fluid control valve 16 may be any suitable type of electrically controlled, on-off valve which can be controlled by the microprocessor 24 or other control device. Preferably, the valve 16 is similar to valve 12 in that it may be a modified, commercially available, six-port slider plate valve which is pneumatically actuated between a deactive position and an activated position. A solenoid valve (not shown), controlled by the microprocessor 24, may control the supply of pneumatic fluid such as instrument air to the valve 16 to cause the movement of the valve between its two positions.

The fluid control valve 16 may include a slider plate 80 movable in a body 82 between the two positions of the valve. The slider plate 80 may include a first groove or passage 84 in one surface of the slider plate 80. A second groove or passage 86 may extend axially in the opposite surface of the slider plate 80 as shown. A through-bore or passage 88 extends between the two surfaces of the slider plate 80.

The body 82 of the fluid control valve 16 may include six ports 90, 92, 94, 96, 98 and 100. The ports 90, 92 and 94 are positioned in one side of the body 82 and the ports 96, 98 and 100 are positioned in the opposite side of the body 82 as shown.

The fluid control valve 16 is modified by eliminating or blocking the ports 90 and 96 which are diametrically opposite to each other as shown. These ports 90 and 96 may be rendered inactive by inserting suitable plugs 102 therein.

In the deactive or "off" position of the valve 16, shown in FIG. 1, the passage 84 connects the ports 90 and 92, and thus is inactive since port 90 is plugged. The passage 86 connects the ports 96 and 98, and is also inactive in the "off" position since port 96 is plugged. The through-bore or passage 88 in the slider plate 80 connects the ports 94 and 100.

Figure 3:
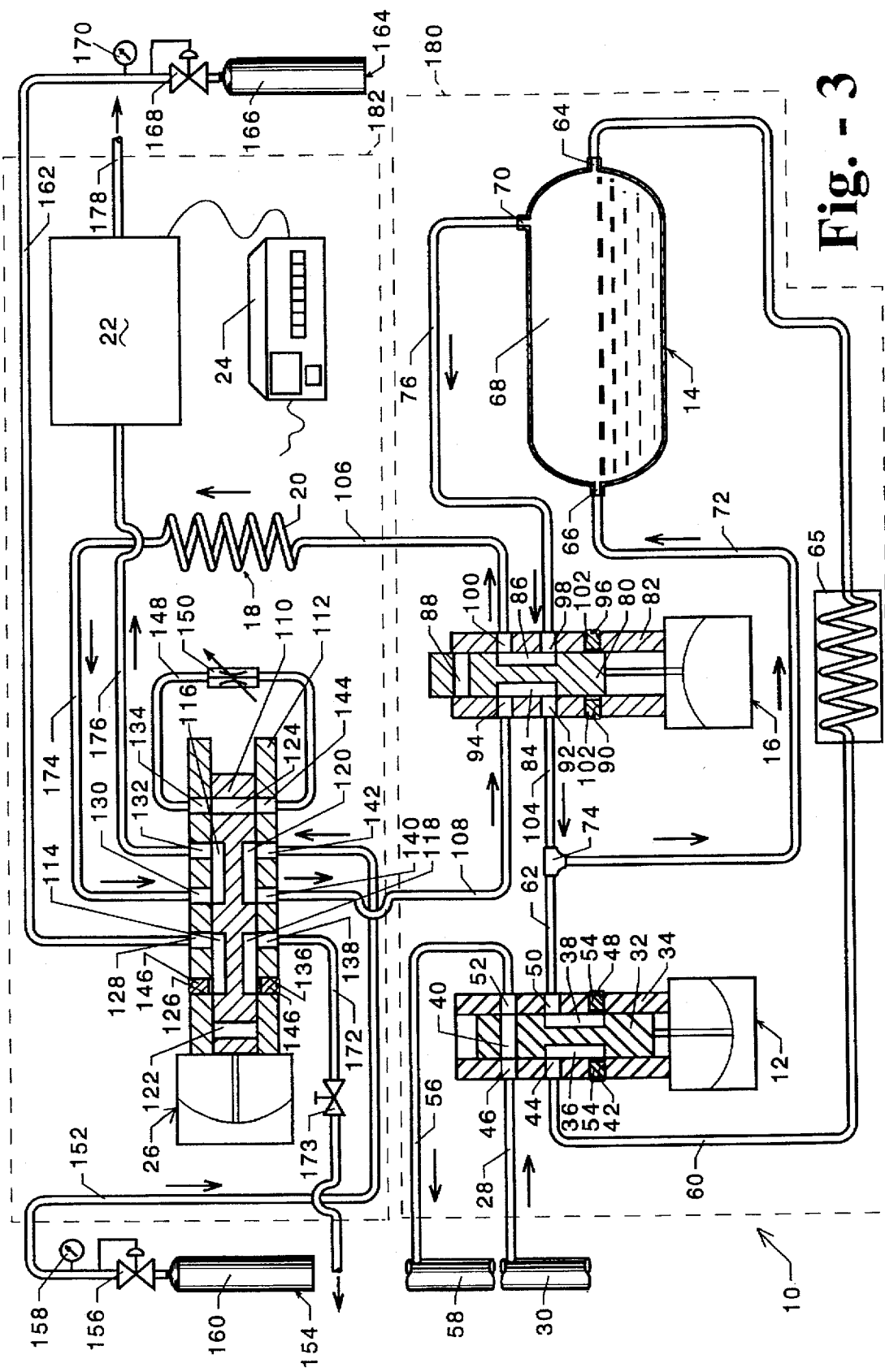
FIG. 3 is a schematic diagram of the monitoring system shown in FIG. 1 showing the positions of the valves and flow through the system during a third stage of operation of the system.

When the valve 16 is actuated into its activated, or "on" position, shown in FIG. 3, the slider plate 80 is extended outwardly, upwardly as viewed in the drawings, so that the passage 84 connects the ports 92 and 94 and passage 86 connects the ports 98 and 100. The ports 90 and 96 are blocked and the through-bore or passage 88 is not in communication with any of the ports as shown.

A carrier gas line 104 is connected at one end to the port 92 of the fluid control valve 16 and at its other end to the tee 74 connected to the lines 62 and 72. The gas flow line 76 from the gas outlet port 70 of the head space chamber 14 is connected to the port 98 of the valve 16. A line 106 from the separation unit 18 is connected to port 100 of the valve 16. A line 108 is connected at one end to the port 94 of the valve 16 and extends to the backflush valve 26.

The backflush valve 26 may be any suitable type of electrically controlled, on-off valve which can be controlled by the microprocessor 24 or other control device. Preferably, the valve 26 is a modified, commercially available, ten-port slider plate valve which is pneumatically actuated between a deactive position and an activated position. A solenoid valve (not shown), controlled by the microprocessor 24, may control the supply of pneumatic fluid such as instrument air to the valve 26 to cause the movement of the valve 26 between its two positions. Alternatively, an electrically actuated rotary valve may be used.

The backflush valve 26 may include a slider plate 110 movable in a body 112 between the two positions of the valve. The slider plate 110 may include a two axially extending grooves or passages 114 and 116 in one surface of the slider plate 110. Two additional grooves or passages 118 and 120 may extend axially in the opposite surface of the slider plate 110 as shown. A first through-bore or passage 122 extends between the two surfaces of the slider plate 110 adjacent one end thereof and a second through-bore or passage 124 extends between the two surfaces of the slider plate 110 adjacent the other end thereof.

The body 112 of the backflush valve 26 may include ten ports 126, 128, 130, 132, 134, 136, 138, 140, 142 and 144. The ports 126, 128, 130, 132 and 134 are positioned in one side of the body 112. The ports 136, 138, 140, 142 and 144 are positioned in the opposite side of the body 112 as shown.

The backflush valve 26 is modified by eliminating or blocking the ports 126 and 136 which are diametrically opposite to each other as shown. These ports 126 and 136 may be rendered inactive by inserting suitable plugs 146 therein.

In the active, or "on" position of the backflush valve 26, shown in FIG. 1, the passage 114 connects the ports 128 and 130, and the passage 116 connects the ports 132 and 134. Also, in the active or "on" position, passage 118 connects the ports 138 and 140, and the passage 120 connects the ports 142 and 144. The through-bore or passage 122 extends between the plugged ports 126 and 136 in the active or "on" position of the backflush valve 26 and is inactive. The through-bore or passage 124 is out of communication with all of the ports as shown and is also inactive.

When the backflush valve 26 is actuated into its deactive or "off" position, shown in FIG. 3, the slider plate 110 is withdrawn inwardly, to the left as viewed in the drawings, so that the passage 114 in the slider plate 110 connects the ports 126 and 128 and passage 118 connects the ports 136 and 138. As the ports 126 and 136 are plugged, the passages 114 and 118 are not active in the "off" position of the backflush valve 26. The through-bore or passage 122 is out of communication with any of the ports and is thus not active in the inactive or "off" position of the backflush valve 26. Also, in the deactive or "off" position of the backflush valve 26, the passage 116 provides communication between the ports 130 and 132 and the passage 120 provides communication between ports 140 and 142. The through-bore or passage 124 provides communication between the two diametrically opposed ports 134 and 144.

The line 108 from the fluid control valve 16 is connected to port 140 of the backflush valve 26. A loop line 148, containing an adjustable flow restrictor 150 has one end connected to port 134 and its other end connected to the port 144 of the backflush valve 26. Any suitable type of adjustable flow restrictor 150 may be used such as a needle valve or the like.

One end of a carrier gas in-feed line 152 is connected to a source 154 of a suitable carrier gas. The other end of the carrier gas in-feed line 152 is connected the port 142 of the backflush valve 26. The carrier gas in-feed line 152 may include a pressure regulator 156 to control the pressure of the incoming carrier gas, and a pressure gauge 158 to provide an indication of the pressure. The carrier gas may be any suitable type of gas which will not react with any components of the sample stream, does not contain any of the components for which the analysis is being conducted, and will not interfere with the detection of the particular species by the detector 22. By way of example, for most applications, the carrier gas may be a suitable inert gas such as highly purified helium gas which may be provided in a suitable storage tank 160.

A purging gas in-feed line 162 is connected to a source 164 of purging gas to be used for backflushing the chromatographic column 20. The purging gas in-feed line 162 is connected at its other end to the backflush valve 26 at the port 128. The purging gas should be the same gas as the carrier gas and preferably come from the same source in which case the inlet end of line 162 may be connected to the line 152 at a tee positioned down stream of the pressure regulator 156. Alternatively, however, the purging gas may have its own source as shown such as a tank 166 to which the line 162 is connected. In such case, the line 162 may be provided with a pressure regulator 168 and a pressure gauge 170 as shown.

A vent line 172 containing a flow restrictor valve 173 extends from the port 138 of the backflush valve 26 to a suitable vent which may include a scrubber (not shown.

A line 174 extends from the port 130 of the backflush valve 26 to the outlet end of the separating unit 18. The separating unit 18 serves to spatially separate the various gaseous species carried by the carrier gas from the head space chamber 14 during the sample analysis cycle of the system. As indicated above, the separating unit 18 may comprise a chromatographic column, or a series of such columns, which may be adapted to specifically separate the particular species involved. Such chromatographic columns, or the components to make such columns are commercially available. One such commercial source is Alltech Associates of Deerfield, Ill.

A gaseous sample feed line 176 extends from the port 132 of the backflush valve 26 to the detector 22. A vent line 178, extending from the detector 22, may be connected to a suitable vent, including a scrubber (not show), to provide for exhaust of the gaseous sample from the detector 22. The type of detector used depends upon the particular species which is monitored. The detector should have the capability of sensing the particular desired species at the appropriate levels of concentration in the carrier gas. Examples of detectors which may be used include photoionization detectors, flame ionization detectors, and thermal conductivity detectors.

The sample inlet valve 12, fluid control valve 16 and head space chamber 14, and associated piping, should be contained in a separate sampling enclosure or housing as indicated by the dotted line 180. The enclosure or housing 180 may be heated by a suitable type of heater (not shown) to maintain the sample at an elevated temperature. The backflush valve 26, separation unit 18 and detector 22, and associated piping, should be contained in a separate analytical enclosure or housing as indicated by the dotted line 182. This enclosure or housing 182 may also be heated by a suitable heater to maintain the gaseous sample at a constant temperature and ensure accuracy of the analytical measurement. The use of the separate enclosures 180 and 182 is desirable since is some instances it may be necessary to maintain the chromatographic column 20 at a temperature higher than can be tolerated in the head space chamber 14.

In operation, when the system 10 is in the "inactive" position, between the analytical cycle and before the replenishment of the liquid sample in the head space chamber 14, the valves 12, 16 and 26 are positioned as shown in FIG. 1. In such position, the sample inlet control valve 12 and the fluid control valve 16 are in their "off" position, and the backflush valve 26 is in its "on" position. With the valves 12, 16 and 26 so positioned, the liquid sample from the process stream flows from the process line 30 though the line 28 to the sample inlet control valve 12, enters the port 46, passes through the passage 40 and exits the valve 12 through the port 52 into the sample return line 56 which returns the liquid sample to the line 58 of the process stream. At the same time, carrier gas flows from its source 154 through the line 152 to the port 142 of the backflush valve 26. The carrier gas flows through the passage 120 in the valve 26 and out through the port 144 into the loop 148 containing the flow restrictor 150 and back into the valve 26 through the port 134. The carrier gas continues through the passage 116 in the backflush valve 26, out of the valve 26 though port 132 into line 176 wherein it passes to the detector 22 and exits the detector 22 by means of line 178, thereby maintaining continuous flow of the carrier gas to the detector 22. As the carrier gas is under a sufficient pressure to pass through the separation unit 18 during analysis, the flow restrictor 150 serves to reduce the flow rate of the carrier gas by an amount substantially equal to the reduction in the flow rate which occurs when the gas passes thorough the separation unit 18. This ensures that the flow rate of the carrier gas through the detector 22 during this cycle is substantially the same as during the analysis cycle when the carrier gas is passing through the separation unit 18.

Also during this period of time, the backflush gas flow from its source 164 through the line 162 into the backflush valve 26 through the port 128, passes through the passage 114, and exits the valve 26 though the port 130 into the line 174. The line 174 is connected to the outlet of the chromatographic column 20 of the separating unit 18 so that the backflush gas flows backwardly though the column 20 into line 106 to the fluid control valve 16. The backflush gas then flows into the valve 16 through the port 100, through the passage 88 and out of the valve 16 through the port 94 into the line 108 to the backflush valve 26. The backflush valve 26 directs the backflush gas entering the valve from the line 108 through port 140, through the passage 118, and out through the port 138 into the vent line 172.

Thus in the non-sampling, non-analyzing position of the system 10, the sample liquid from the process stream passes through the sample inlet control valve 12 which serves to immediately return the liquid sample to the process stream. Also, in this position, the backflush valve 26 serves to direct carrier gas through the detector 22 to remove residual sample. The backflush valve 26, in conjunction with the fluid control valve 16, directs a backflush gas backwardly through the chromatographic column 20 to backflush the column 20.

The first step at the start of a sampling cycle is to replenish the liquid sample in the head space chamber 14. This is accomplished by actuating the sample inlet control valve 12 into its "on" position while the fluid control valve remains in the "off" position and the backflush valve remains in its "on" position as shown in FIG. 2. With the sample inlet control valve 12 in such position, a liquid sample from the process stream flows under pressure from the line 30 in the process stream through the line 28 into the port 46 of the valve 12. The liquid sample continues to flow through the passage 36 and out of the valve 12 though the port 44 into the line 60 through which it flows to the head space chamber 14 and enters the chamber through the inlet port 64. The heat exchanger 65 in the line 60 helps to raise the temperature of the incoming liquid sample to the point at which it can be maintained at the desired temperature by the thermostated housing 180. The incoming liquid sample replaces the liquid previously in the head space chamber 14 and fills the chamber up to the level of the outlet port 66. Excess liquid sample passes out of the chamber 14 through the outlet port 66 into the line 72 where it flows though the tee 74 into line 62 and back into the sample inlet control valve 12 through port 50. The excess liquid then passes though the passage 38 in the valve 12, out through the port 52 into the return line 56 through which it flows to the line 58 of the process stream and reenters the process stream. During this portion of the sampling cycle, the fluid control valve 16 and backflush valve 26 remain in their previous position so that the flushing of the detector 22 and the backflushing of the chromatographic column 20 continue.

The sample inlet control valve 12 remains in its "on" position for a sufficient amount of time to ensure that the liquid sample in the head space chamber 14 is completely replenished. Generally, to ensure reliable analysis, the sample inlet control valve 12 may remain "on" until at least three volumes of new liquid sample have passed through the head space chamber 14, and preferably at least five volumes have passed through. The amount of time during which the sample inlet control valve remains in its "on" position may be determined by calculations using the known volume of the liquid portion of the head space chamber 14 and the flow rate of the incoming liquid sample.

After the liquid sample in the head space chamber 14 has been sufficiently replenished, the sample inlet control valve 12 is actuated back into its "off" position, halting the flow of the incoming liquid sample to the head space chamber 14, and permitting the fresh liquid sample in the chamber 14 to come to rest. The valves 12, 16 and 26 remain in their positions indicated in FIG. 1, with the liquid sample in the head space chamber 14 remaining at rest for a sufficient period of time to permit the gaseous phase of the volatile gaseous species escaping from the liquid into the area 68 above the liquid level in the head space chamber 14 to come into partial or complete equilibrium. Complete equilibrium may not be required depending upon the concentration of the species in the liquid since repetitive results will be achieved due to the controlled conditions of the system.

After the gaseous phase of the volatile species in the newly replenished liquid has escaped from the liquid into the area 68 above the liquid, and has come into partial or complete equilibrium, the analytical portion of the monitoring cycle may be initiated. When it is desired to perform an analysis, the backflush valve 26 is actuated into its "off" position, followed shortly by the actuation of the fluid control valve 16 into its "on" position. The sample control valve 12, is maintained in its "off" position. The positions of the respective valves 12, 16 and 26 at this point in the cycle are shown in FIG. 3. While the backflush valve 26 and fluid control valve 16 may be actuated substantially simultaneously, a slight time delay before the actuation of the fluid control valve 16 is preferable since such delay will permit the start of the flow of carrier gas forwardly through the column 20 by directing the carrier gas through line 108 to the valve 16, into the valve 16 through port 94, through passage 88, out of the valve 16 through port 100 into line 106 to the column 20.

With the valves positioned as shown in FIG. 3 to initiate the analytical portion of the cycle, carrier gas flows from its source 154 through the line 152 and through the port 142 of the backflush valve 26. The carrier gas continues to flow through the passage 120 of the valve 26 and exits through port 140 into the line 108 to the fluid control valve 16. The carrier gas then passes into the fluid control valve 16 through port 94, passes through the passage 84 and exits the valve through the port 92 into the line 104, through the tee 74 into line 72 to the outlet port 66 of the head space chamber 14. The carrier gas enters the chamber 14 through the outlet port 66 and sweeps over the surface of the liquid sample in the chamber 14 and carries the gaseous phase in the head space area 68 containing the selected species out through the gas outlet 70 into the line 76 The carrier gas carries the gaseous phase from the head space area 68 along with any gaseous phase present in line 76 to the fluid control valve 16 where it enters the valve 16 through the port 98, passes through passage 86, and exits the valve 16 through the port 100 into the line 106. The volume of the head space area 68 and the internal volume of the length of the line 76 provides a known fixed volume of gaseous sample which passes through the chromatographic column 20 and the detector 22.

The line 106 directs the carrier gas and gaseous species to the separating unit 18 which contains a suitable species separating member such as the chromatographic column 20. The chromatographic column 20 spatially separates the various gaseous species so that they exit the separating unit 18 into line 174 at different times. The carrier gas with the separated species then flows through the line 174 into the port 130 of the backflush valve 26, passes through the passage 116, and exits the valve 26 through port 132 into the line 176 to the detector 22. The carrier gas with the separated species passes through the detector 22 which detects the presence of the various species and provides an electrical signal, or other indication, proportional to the concentration of the particular species detected. This signal may then be converted by the microprocessor 24 to provide an output of the actual concentration of the species.

After an appropriate period of time sufficiently long to ensure that the carrier gas has carried the selected gaseous species from the head space chamber 14 to the detector 22, the backflush valve 26 is returned to its "on" position and the fluid control valve 16 returned to its "off" position as shown in FIG. 1, ready for the start of the next cycle.

Figure 4:
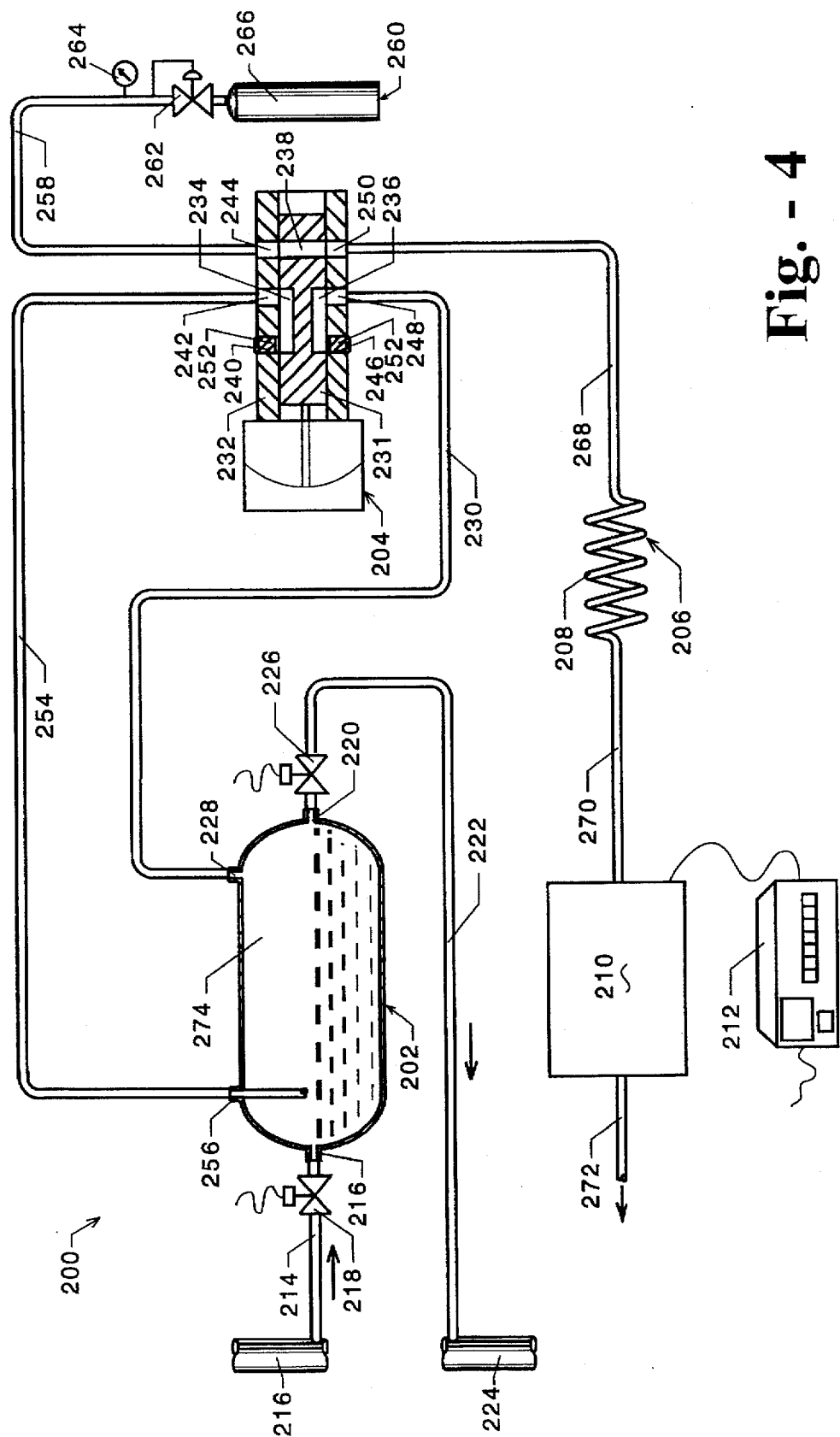
FIG. 4 is a schematic diagram of a second embodiment of a monitoring system incorporating the principals of the present invention.

FIG. 4 shows a modified system 200 constructed according to the principals of the present invention. Similar to the system of FIGS. 1–3, system 100 includes a head space chamber 202 in which the sample from the process is temporarily held to permit the volatile species to escape from the liquid matrix into a gaseous phase and reach partial or complete equilibrium, and a fluid control valve 204 which directs flow of a carrier gas to the head space chamber 202 to carry the gaseous phase in the head space chamber 202 to a separation unit 206 such as a chromatographic column 208 for physically separating the subject species and then to a detector 210 for detecting and measuring the presence and amount of the particular species. A microprocessor 212 may be provided to control the sampling operation and receive signals from the detector 210. Although not shown in FIG. 4, a backflush control valve, similar to the backflush control valve 26 described in connection with the system 10 shown in FIG. 1–3, may be provided in conjunction with the chromatographic column 208 to control the flow of a backflush gas to the column 208 during the intervals between analysis. As an alternative, the system 100 may be set up so that the carrier gas containing the gaseous species passes directly to the detector 210.

More specifically, in the system 200 shown in FIG. 4, a sample input line 214 has one end connected to a source such as a line 216 of the process stream, or other suitable portion of the process equipment, containing the liquid to be sampled. The other end of the sample input line 214 is connected to an inlet port 216 of the head space chamber 202. A shut-off valve 218 is positioned in the sample input line 214 at a point adjacent to the inlet port 216. This valve 218 may be any type of suitable electrically operated shut-off valve such as a solenoid actuated, on-off switching valve which is controlled by the microprocessor 212.

The head space chamber 202 is provided with a liquid outlet port 220 to which one end of a sample return line 222 is connected. The other end of the sample return line 222 is connected to the source of the liquid such as a line 224 or other suitable portion of the process equipment at a point which is at a lower pressure than the point from which the sample is taken, but which may be greater than atmospheric pressure. A shut-off valve 226 is positioned in the sample outlet line 222 at a point adjacent to the outlet port 220. This valve 226 may be the same as the valve 218 and may be any type of suitable electrically operated shut-off valve such as a solenoid actuated on-off switching valve which is controlled by the microprocessor 212.

A gas outlet port 228 is provided in the head space chamber similar to the gas outlet port 70 in the embodiment of FIGS. 1–3. A gas flow line 230 has one end connected to the gas outlet port 228 and its other end connected to the fluid control valve 204.

The fluid control valve 204 may be the same as the valve 16 of the embodiment of FIGS. 1–3. Thus the valve 204 may be any suitable type of electrically controlled, on-off valve which can be controlled by the microprocessor 212 or other control device. Preferably, the valve 204 is a commercially available, six-port slider plate valve which is pneumatically actuated between a deactive position and an activated position. A solenoid valve (not shown), controlled by the microprocessor 212, may control the supply of pneumatic fluid such as instrument air to the valve 204 to cause the movement of the valve 204 between its two positions.

The fluid control valve 204 may include a slider plate 231 movable in a body 232 between the two positions of the valve. The slider plate 231 may include a first groove or passage 234 in one surface of the slider plate 231. A second groove or passage 236 may extend axially in the opposite surface of the slider plate 231 as shown. A through-bore or passage 238 extends between the two surfaces of the slider plate 231.

The body 232 of the fluid control valve 204 may include six ports 240, 242, 244, 246, 248 and 250. The ports 240, 242 and 244 are positioned in one side of the body 232 and the ports 246, 248 and 250 are positioned in the opposite side of the body 232 as shown.

The fluid control valve 204 is modified by eliminating or blocking the ports 240 and 246 which are diametrically opposite to each other as shown. These ports 240 and 246 may be rendered inactive by inserting suitable plugs 252 therein.

In the deactive or "off" position of the valve 16, shown in FIG. 4, the passage 234 connects the ports 240 and 242, and thus is inactive since port 240 is plugged. The passage 236 connects the ports 246 and 248, and is also inactive in the "off" position since port 246 is plugged. The through-bore or passage 238 in the slider plate 231 connects the ports 244 and 250.

When the valve 204 is actuated into its activated, or "on" position, the slider plate 231 is extended outwardly, to the right as viewed in FIG. 4, so that the passage 234 connects the ports 242 and 244 and passage 236 connects the ports 248 and 250. The ports 240 and 246 are blocked and the through-bore or passage 238 is not in communication with any of the ports as shown.

The gas flow line 230 is connected to the port 24 of the fluid control valve 204. A carrier gas line 254 is connected at one end to the port 242 of the fluid control valve 204 and at its other end to a carrier gas inlet port 256 in the head space chamber 202. As will be noted from FIG. 4, the carrier gas inlet port 256 is positioned adjacent the end of the chamber 202 opposite the end at which the gas inlet outlet port 228 is located. The gas inlet port 256 and gas outlet port 228 are thus spaced apart in the direction of the axis of the head space chamber 202 to permit the flow of the carrier gas to pass over the upper level of the liquid.

One end of a carrier gas in-feed line 258 is connected to the port 244 of the fluid control valve 204. The other end of the carrier gas in-feed line 258 is connected to a source 260 of a suitable carrier gas. Similar to the embodiment of FIGS. 1–3, the carrier gas in-feed line 258 may include a pressure regulator 262 and a pressure gauge 264. As mentioned above, the carrier gas may be any suitable type of gas which will not react with any components of the sample stream, does not contain any of the components for which the analysis is being conducted, and will not interfere with the detection of the particular species by the detector 210 By way of example, for most applications, the carrier gas may be a suitable inert gas such as highly purified helium gas which may be provided in a suitable storage tank 266.

A gas sample line 268 has one end connected to the port 250 of the fluid control valve 204 and its other end connected to the inlet of the chromatographic column 208 of the separating unit 206. A line 270 has one end attached to the outlet of the chromatographic column 206 and its other end connected to the detector 210. A vent line 272, extending from the detector 210, may be connected to a suitable vent, including a scrubber (not show), to provide for exhaust of the gaseous sample from the detector 210. The detector 210 may be the same as the detector 22 previously described in connection with the system 10.

In the operation of the system 200 of FIG. 4, when it is desired to replenish the liquid in the head space chamber 202, both the shut-off valves 218 and 226 are actuated into their open position, while the fluid control valve 204 remains in its "off" position. With this arrangement, sample liquid will flow from its source 216 through line 214 and the valve 218 into the head space chamber 203 through port 216. The excess liquid will exit the head space chamber 202 through the port 220 and pass through the valve 226 and return line 222 back into the process stream at the point 224. With the fluid control valve 204 in its "off" position, liquid will not be able to flow in the lines 230 and 254 since the lines are blocked. Also, with the fluid control valve 204 in the "off" position, carrier gas will flow from its source 260 through line 258 into the fluid control valve 204 through port 244. The carrier gas will pass through the passage 238 in the valve 204 and exit the valve 204 through port 250 into the line 268. From line 268, the carrier gas passes through the chromatographic column 208 to the detector 210 and exits the detector 210 through the vent line 272. This provides a continual flow of carrier gas to the detector 210.

After the liquid sample in the head space chamber 202 has been sufficiently replenished, the shut-off valves 218 and 226 are actuated back into their "off" position, halting the flow of the incoming liquid sample to the head space chamber 202, and preventing flow of the liquid out of the chamber 202, permitting the fresh liquid sample in the chamber 14 to come to rest.

With the liquid in the head space chamber 202 at rest, after the gaseous phase of the volatile species in the newly replenished liquid has escaped from the liquid into the area 274 above the liquid, and has come into partial or complete equilibrium, the analytical portion of the monitoring cycle may be initiated. When it is desired to perform an analysis, the fluid control valve 204 is actuated into its "on" position. In this position, the carrier gas will flow from its source 260 through line 258 into the valve 204 through port 244. The carrier gas passes through passage 234 and exits the valve 204 through port 242 into the line 254. The carrier gas flows in line 254 to the head space chamber 202 where it enters the chamber through port 256 and sweeps over the surface of the liquid sample in the chamber 202 and carries the gaseous phase in the head space area 68 containing the selected species out through the gas outlet 228 into the line 230. The carrier gas carries the gaseous phase from the head space area 274, along with any gaseous phase present in line 230, to the fluid control valve 230 where it enters the valve 230 through the port 248, passes through passage 236, and exits the valve 204 through the port 250 into the line 268 to the chromatographic column 208. The volume of the head space area 274 and the internal volume of the length of the line 230 provides a known fixed volume of gaseous sample which passes through the chromatographic column 20 and the detector 22.

The line 268 directs the carrier gas and gaseous species to the separating unit 206 which contains a suitable species separating member such as the chromatographic column 208. The chromatographic column 208 spatially separates the various gaseous species so that they exit the separating unit 206 into line 270 at different times. The carrier gas with the separated species then flows through the line 270 to the detector 210. The carrier gas with the separated species passes through the detector 210 which detects the presence of the various species and provides an electrical signal, or other indication, proportional to the concentration of the particular species detected. This signal may then be converted by the microprocessor 212 to provide an output of the actual concentration of the species.

After an appropriate period of time sufficiently long to ensure that the carrier gas has carried the selected gaseous species from the head space chamber 202 to the detector 210, the fluid control valve 204 is returned to its "off" position ready for the start of the next cycle.

With the arrangement shown in FIG. 4, the two shut-off valves 218 and 226, which are positioned close to the inlet port 216 and outlet port 220 respectively, serve to isolate the liquid sample in the head space chamber and minimize the amount of liquid sample that comes to rest in the piping outside of the chamber 202. By providing the gas inlet port 256 separate from the liquid inlet port 216, the carrier gas does not have to pass through the liquid sample during any point of its travel, which could result in stripping of species therefrom.

The monitoring cycle, as described above in connection with both systems 10 and 200 includes replenishing the liquid in the head space chamber 14 or 202, halting the flow of the sample liquid thereto and permitting the volatile species in the sample liquid to escape therefrom into their gaseous phase and reach partial or complete equilibrium prior to the introduction of the carrier gas into the chamber 14 or 202, and then sweeping a carrier gas over the liquid sample in the chamber 14 or 202 to carry the gaseous species to the detector 22 or 210.

While the invention has been described above with reference to various embodiments thereof, it is apparent that many changes, modifications and variations can be made without departing from the concepts disclosed herein. Accordingly, it is intended to embrace all such changes, modifications and variations that fall within the spirit and broad scope of the appended claims.

What is claimed is:

1. A method of monitoring a volatile species in a liquid comprising the steps of:
    a. providing a flow of a liquid containing volatile species to be monitored from a source thereof to a head space chamber at a temperature effective to aid evaporation,
    b. interrupting said flow of said liquid to said chamber to provide a volume of liquid in said chamber and permitting the violatile species to escape from said liquid in said chamber into a gaseous phase creating a gaseous species while in said chamber, and
    c. subsequently sweeping a carrier gas over the surface of said liquid volume prior to the gaseous species in the chamber and the liquid reaching complete equilibrium while said liquid flow is interrupted to carry the gaseous species to a detector for monitoring the volatile species.

2. The method of claim 1 wherein the liquid is taken from a point in its source where said liquid is at a pressure greater than atmospheric.

3. The method of claim 2 wherein said liquid is taken from its source at a pressure of at least 5 psig.

4. The method of claim 2 further comprising returning the liquid in said head space chamber to its source at a point that has a pressure greater than atmospheric pressure.

5. The method of claim 2 further comprising returning the liquid in said head space chamber to its source at a point that has a pressure greater than atmospheric pressure and less than the pressure at which the liquid taken.

6. The method of claim 1 further comprising discontinuing the flow of carrier gas over the liquid, and thereafter resuming the flow of the liquid to said head space chamber to replenish the liquid therein.

7. The method of claim 1 further comprising discontinuing the flow of carrier gas over the liquid volume, and thereafter repeating the steps of claim 1.

8. The method of claim 1 wherein said liquid in said chamber has a horizontal upper surface, and said sweeping of said carrier gas sweeps said carrier gas over said horizontal surface.

9. The method of claim 1 wherein said flow is provided to said chamber by opening a valve in an inlet line connected to said chamber and opening a valve in an outlet line from said chamber, and said flow is interrupted by closing said valves in said inlet line and said outlet line.

10. A system for monitoring of a volatile species in a liquid comprising:
    a. a head space chamber in which volatile species in a liquid escape from the liquid into a gaseous phase above the liquid,
    b. means comprising a first valve arrangement for controlling a flow of the liquid to be sampled from a source thereof to said head space chamber at a temperature effective to aid evaporation,
    c. a detector for detecting the presence of the volatile species in its gaseous form,
    d. a source of a carrier gas,
    e. a second valve arrangement for controlling a flow of said carrier gas from its source to said head space chamber, and means comprising a controller for actuating the first valve arrangement to provide a fixed volume of said liquid from its source to said head space chamber and thereafter halting the flow thereto, and actuating the second valve arrangement after the halting of the flow of the liquid by said first valve arrangement to permit flow of said carrier gas to said head space chamber to carry the gaseous phase of the volatile species to said detector prior to the gaseous phase and the liquid sample reaching complete equilibrium.

11. The system of claim 10 wherein said liquid to be sampled is taken from its source at a point where the pressure of said liquid is greater than atmospheric.

12. The system of claim 11 wherein said liquid at the point at which it is taken from its source has a pressure of at least 5 psig.

13. The system of claim 11 further including a return flow path for the liquid from the head space chamber back to its source at a point that has a pressure greater than atmospheric, said first valve arrangement providing for flow through said return flow path when actuated to permit flow to said head space chamber and halting flow back to said source when flow to said chamber is halted.

14. The system of claim 13 wherein the pressure of said source at the point at which the liquid is returned has a pressure less than the pressure of the source at the point at which the liquid is taken from the source.

15. The system of claim 10 wherein said controller causes the actuation of said second valve arrangement to halt the flow of carrier gas to said head space chamber and thereafter causes the action of the first valve arrangement cause the liquid sample to again flow to said chamber to replenish the liquid therein.

16. The system of claim 10 wherein said head space chamber has a horizontal axis of elongation, said liquid in said head space chamber presenting a horizontal surface, and said flow of said carrier gas carries said gas over said horizontal surface of said liquid.

17. The system of claim 10 wherein said controller repeats the step f. to provide for repetitive monitoring.

18. The system of claim 10 wherein said head space chamber has a liquid inlet port and a liquid outlet port, and further comprising a liquid inlet line connected to said liquid inlet port and a liquid outlet line connected to said liquid outlet port, said first valve arrangement including a first valve in said liquid inlet line and a second valve in said liquid outlet line.

19. The system of claim 18 wherein said first valve is positioned adjacent said liquid inlet port and said second valve is positioned adjacent said liquid outlet port.

20. The system of claim 18 wherein said head space chamber includes a carrier gas inlet port and a carrier gas outlet port spaced from each other and separate from said liquid inlet port and said liquid outlet port.

* * * * *